United States Patent
Sachdeva et al.

(10) Patent No.: US 7,422,430 B2
(45) Date of Patent: *Sep. 9, 2008

(54) METHOD AND APPARATUS FOR ORTHODONTIC APPLIANCE OPTIMIZATION

(75) Inventors: Rohit Sachdeva, Plano, TX (US); Rudger Rubbert, Berlin (DE); Thomas Weise, Berlin (DE); Friedrich Riemeier, Berlin (DE)

(73) Assignee: OraMetrix Inc., Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/847,004

(22) Filed: May 17, 2004

(65) Prior Publication Data

US 2004/0214129 A1    Oct. 28, 2004

Related U.S. Application Data

(63) Continuation of application No. 09/560,130, filed on Apr. 28, 2000, now Pat. No. 6,736,638, which is a continuation-in-part of application No. 09/552,191, filed on Apr. 19, 2000, now abandoned.

(51) Int. Cl.
*A61C 3/00* (2006.01)
(52) U.S. Cl. .............................. 433/24; 433/8
(58) Field of Classification Search .............. 433/24, 433/8
See application file for complete search history.

(56) References Cited

U.S. PATENT DOCUMENTS

| | | | | |
|---|---|---|---|---|
| 4,455,137 A | * | 6/1984 | Diamond | 433/3 |
| 5,011,405 A | * | 4/1991 | Lemchen | 433/24 |
| 5,238,404 A | * | 8/1993 | Andreiko | 433/20 |
| 5,338,198 A | * | 8/1994 | Wu et al. | 433/213 |
| 5,683,243 A | * | 11/1997 | Andreiko et al. | 433/3 |
| 5,879,158 A | * | 3/1999 | Doyle et al. | 433/24 |
| 5,975,893 A | * | 11/1999 | Chishti et al. | 433/6 |
| 6,068,482 A | * | 5/2000 | Snow | 433/223 |
| 6,099,314 A | * | 8/2000 | Kopelman et al. | 433/213 |
| 6,217,325 B1 | * | 4/2001 | Chishti et al. | 433/24 |
| 6,227,851 B1 | * | 5/2001 | Chishti et al. | 433/24 |
| 2002/0025503 A1 | * | 2/2002 | Chapoulaud et al. | 433/24 |

* cited by examiner

*Primary Examiner*—John J Wilson
(74) *Attorney, Agent, or Firm*—McDonnell Boehnen Hulbert & Berghoff LLP

(57) ABSTRACT

A method and apparatus for arch wire receptacle (e.g., brackets, bands, headgear tubes, etc.) optimization includes processing that begins by obtaining a digital model of an orthodontic structure of an orthodontic patient. The processing then continues by retrieving a digital model of an initial arch wire receptacle that was selected from a plurality of digital models of arch wire receptacles. The processing then continues by digitally placing the digital model of the initial arch wire receptacle on a given tooth of the digital model of the orthodontic structure to provide a digital arch wire receptacle placement. The process then proceeds by retrieving a digital model of an arch wire. For the given tooth, the processing continues by digitally modeling a force system on the tooth based on the digital model of the initial arch wire receptacle, the digital arch wire receptacle placement, and the digital model of the arch wire. Having done this, when the force system is not optimal, the force system is modified to achieve an optimal forced system.

10 Claims, 6 Drawing Sheets

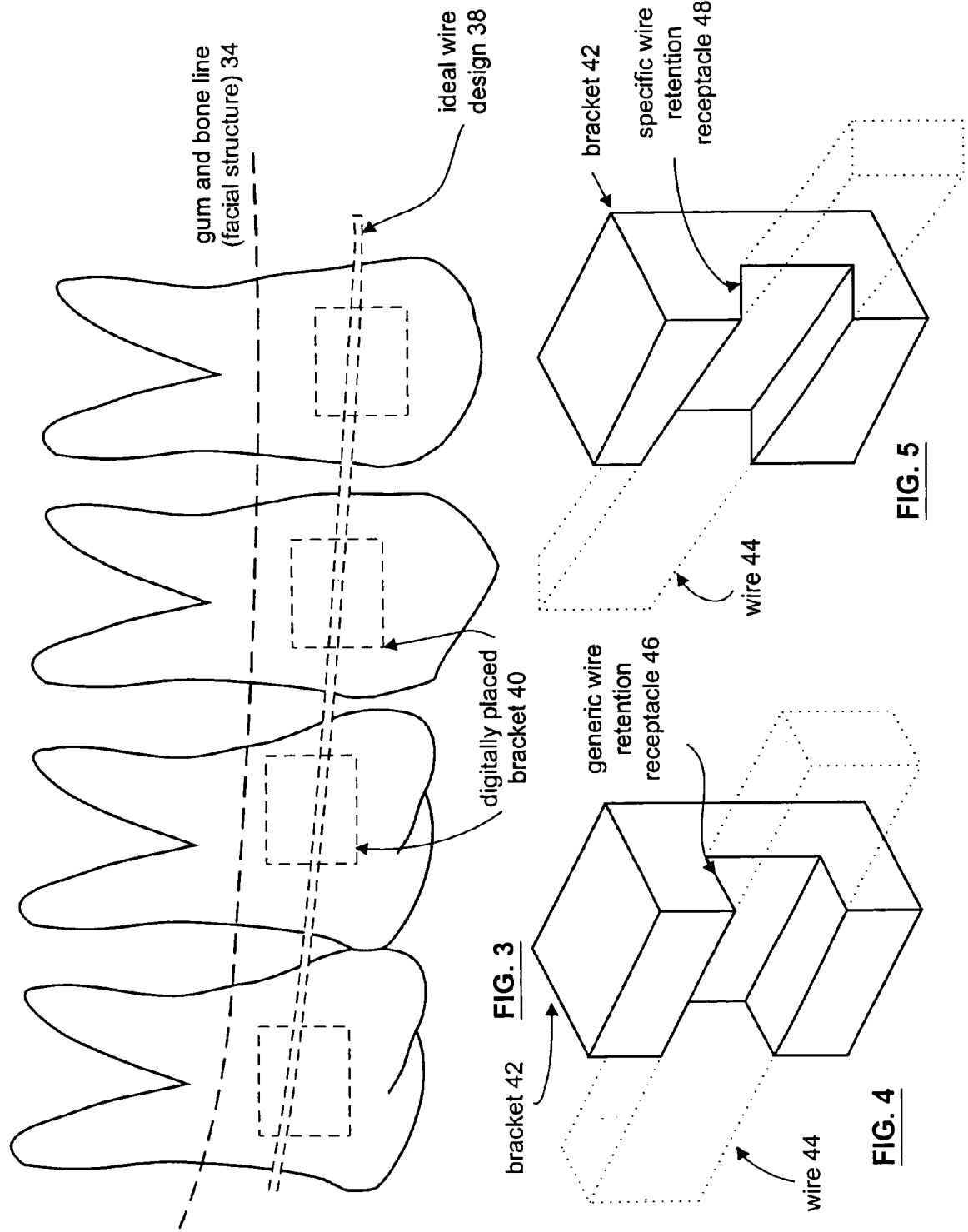

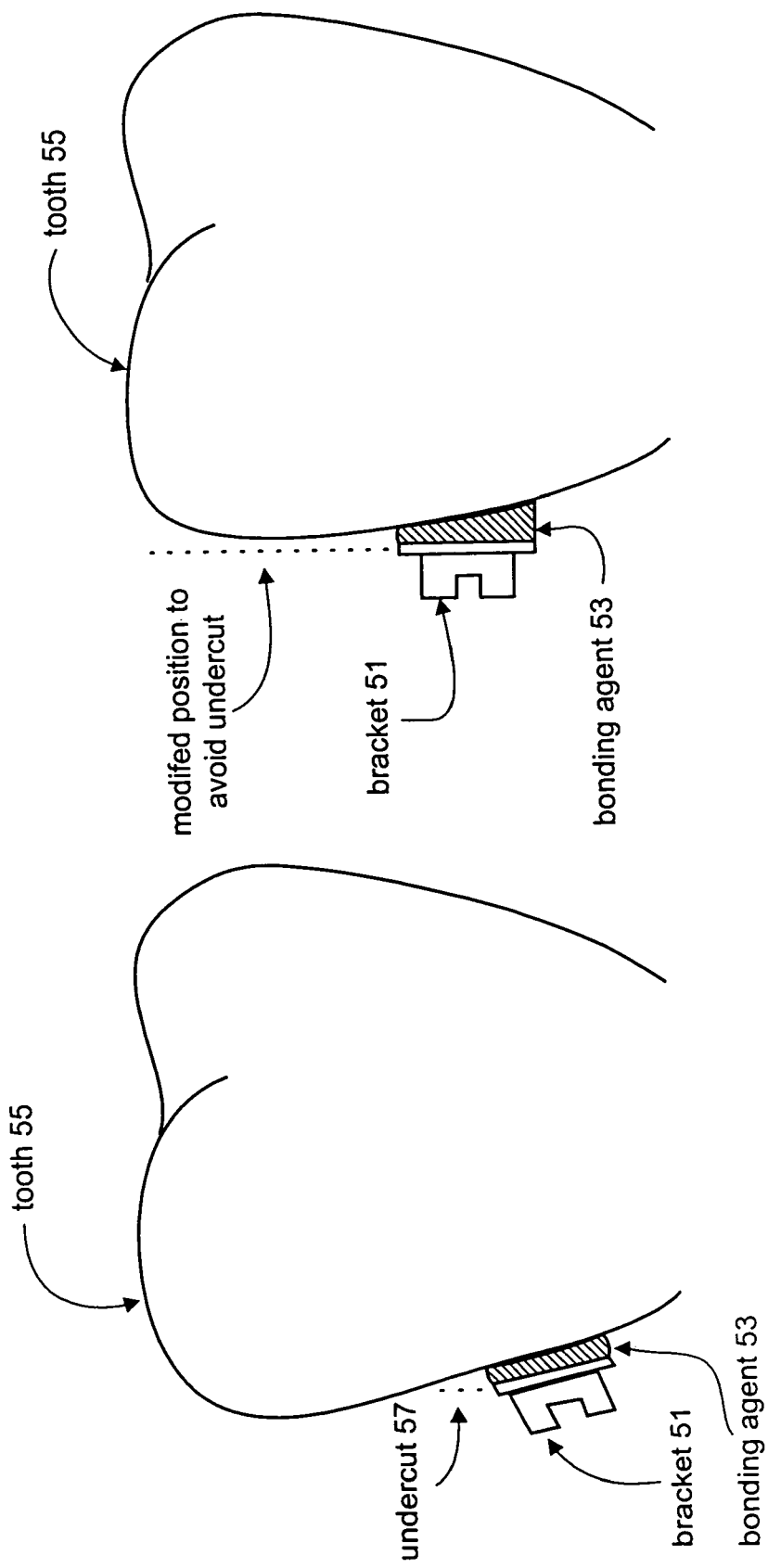

METHOD AND APPARATUS FOR ORTHODONTIC APPLIANCE OPTIMIZATION

This is a continuation of application Ser. No. 09/560,130 filed Apr. 28, 2000, now U.S. Pat. No. 6,736,638, which is a continuation-in-part of Ser. No. 09/552,191 filed Apr. 19, 2000, abandoned.

TECHNICAL FIELD OF THE INVENTION

This invention relates generally to the practice of orthodontics and in particular to a method and apparatus for optimizing arch wire receptacles of an orthodontic apparatus.

BACKGROUND OF THE INVENTION

Orthodontics is known to be the practice of manipulating a patient's teeth to provide better function and appearance. In general, brackets are bonded to a patient's teeth and coupled together with an arch wire. The combination of the brackets and wire provide a force on the teeth causing them to move. Once the teeth move to a desired location and are held in place for a certain period of time, the body adapts bone and tissue to maintain the teeth in the desired location. To further assist in retaining the teeth in the desired, the patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his or her expertise to place the brackets and/or bands on the teeth and then manually bends (i.e., shapes) the arch wire such that a force is asserted on the teeth to reposition the teeth into the desired physical orthodontic structure. As the teeth move towards the desired location, the orthodontist makes continual judgments as to the progress in the treatment, the next step in the treatment (e.g., new bends in the arch wire, repositioning or replacing brackets, is headgear required, etc.) and the success of the previous step.

In general, the orthodontist makes manual adjustments to the arch wire and/or replaces or repositions brackets based on his or her own expert opinion. Unfortunately, in the oral environment, it is impossible, using human sight, to accurately develop a three-dimensional mental image of an orthodontic structure due to the limitations of human sight and the physical structure of a human mouth. In addition, it is humanly impossible to accurately estimate three-dimensional wire bends (with an accuracy within a few degrees and to manually apply such bends to a wire). Further it is humanly impossible to determine an ideal bracket location to achieve the desired orthodontic structure based on mental images. It is also extremely difficult to manually place brackets in the estimated ideal location, and to control bonding agent thickness, ligation forces, manufacturing tolerances, and biological changes. Accordingly, orthodontic treatment is an iterative process, which varies depending on diagnostics, biology, therapeutic approach and appliance system. As such, orthodontic treatment typically requires multiple wire changes, with the type, success, and speed of treatment being very much dependent on the orthodontist's motor skills and diagnostic expertise. As a result of multiple wire changes, patient discomfort is increased as well as treatment costs. As one would expect, the quality of care varies greatly from orthodontist to orthodontist, as does the time to treat a patient.

As described, the practice of orthodontic is very much an art, relying on the expert opinion and judgment of the orthodontist. In an effort to shift the practice of the orthodontic from an art to a science, many innovations have been developed. For example, U.S. Pat. No. 5,518,397 issued to Andreiko, et. al, describes a method of forming an orthodontic brace. Such a method includes obtaining a model of the teeth of a patient's mouth and a prescription of desired positioning of such teeth. The two-dimensional contour of the teeth of the patient's mouth is determined from the model. Calculations of the contour and the desired positioning of the patient's teeth are then made to determine the geometry of an orthodontic appliance (e.g., grooves or slots to be provided in the brackets). Custom brackets including a special geometry have been created for receiving an arch wire to form an orthodontic brace system. Such geometry is intended to provide for the disposition of the arched wire on the bracket in a progressive curvature of a horizontal plane and a substantially linear configuration in a vertical plane. The geometry of the bracket is altered, (e.g., by cutting grooves into the bracket at individual positions and angles and with particular depth) and in accordance with such calculations of the geometry of the patient's teeth. In such a system, the brackets are customized to provide three-dimensional movement of the teeth once the wire, which has a two-dimensional shape, (i.e., linear shape in the vertical plane and curvature in the horizontal plane) is applied to the brackets.

Unfortunately, the current innovations to change the practice of orthodontic from an art to a science have only made limited progress. This is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of a millimeter or less and an angle of a few degrees or less) can cause a different force system (i.e., magnitude of movement and direction of movement) than the desired force system to be applied to the teeth. As such, the tooth will not be repositioned to the desired location.

To assist in the accurate placement of brackets on a tooth, a jig may be utilized. One such jig is disclosed in U.S. Pat. No. 5,368,478 issued to Andreiko, et. al which describes a method for forming jigs for custom placement of orthodontic appliances on teeth. In general, the '478 patent teaches that each jig is provided with a surface conforming to the contour of the tooth to which they are to be mounted. Another surface of the jig engages the bracket to hold it in the proper position and orientation for mounting to the tooth and spaced in relation to the contour surface to precisely locate the jig on the tooth. The jigs are particularly useful in positioning brackets of custom appliances desired to the individual anatomy of the patient and requiring custom positions of the brackets on the teeth. While the '478 patent discloses a method for forming a jig, such jig utilization still keeps the bracket as the focal point of the orthodontic treatment and provides no feedback mechanism regarding actual placement of the bracket. Further, the '478 patent does not allow for variables associated with tooth movement such as static, dynamic, or psychosocial mechanical and/or biological changes.

To achieve optimal orthodontic treatment, the force system applied to each tooth must be optimal. The scientific approach as previously discussed, however, relies on initial diagnostic and orthodontic apparatus design without any means for verification once the initial diagnostics is complete. Once the orthodontic apparatus is designed, the accuracy of all subsequent patient treatment relies on accurate placement of the brackets of the orthodontic structure. If the bracket is not of an optimal design or if the bracket is misplaced, the desired force system on the tooth will not be obtained. As such, orthodontic treatment will not be as accurate as desired and thus will be less than optimal.

Therefore, to further enhance the accuracy of orthodontic treatment a need exists for a method and apparatus that enables optimized arch wire receptacle designs.

BRIEF DESCRIPTION OF THE DRAWINGS

FIG. 3 illustrates a graphical representation of brackets being ideally positioned in accordance with the present invention;

FIG. 4 illustrates an isometric view of a bracket having a generic wire retention receptacle in accordance with the present invention;

FIG. 5 illustrates an isometric view of a bracket including a specific wire retention receptacle in accordance with the present invention;

FIG. 6 illustrates a graphical representation of bracket undercut correction in accordance with the present invention;

DETAILED DESCRIPTION OF A PREFERRED EMBODIMENT

Generally, the present invention provides a method and apparatus for arch wire receptacle (e.g., brackets, bands, headgear tubes, etc.) optimization. Such a method and apparatus includes processing that begins by obtaining a digital model of an orthodontic structure of an orthodontic patient. This may be done in accordance with the teachings of patent application, which is hereby incorporated by reference, entitled "Method and Apparatus for Producing a Three-Dimensional Image of an Orthodontic Patient" filed on Nov. 30, 1999 having a Ser. No. 09/452,034, abandoned. The processing then continues by retrieving a digital model of an initial arch wire receptacle (e.g., a bracket, a band, a headgear tube, etc.) that was selected from a plurality of digital models of arch wire receptacles. Generation of a digital model of an arch wire receptacle is described in application, which is hereby incorporated by reference, entitled "Method and Apparatus for Designing an Orthodontic Apparatus to Provide Tooth Movement" filed on Nov. 30, 1999 having a Ser. No. 09/451,564, now U.S. Pat. No. 6,350,120. The processing then continues by digitally placing the digital model of the initial arch wire receptacle on a given tooth of the digital model of the orthodontic structure to provide a digital arch wire receptacle placement. The process then proceeds by retrieving a digital model of an arch wire. For the given tooth, the processing continues by digitally modeling a force system on the tooth based on the digital model of the initial arch wire receptacle, the digital arch wire receptacle placement, and the digital model of the arch wire. Having done this, when the force system is not optimal, the force system is modified to achieve an optimal force system. The force system includes the effects of bonding pad thickness, bonding agent properties, the arch wire, ligation forces, and biological characteristics (e.g., growth, tooth interference, tooth anatomy). Each of these factors may be adjusted individually or in combination to optimize the force system. With such a method and apparatus, optimal force systems given orthodontic parameter constraints may be obtained without the limitations of prior art orthodontic practices.

Figure 1:
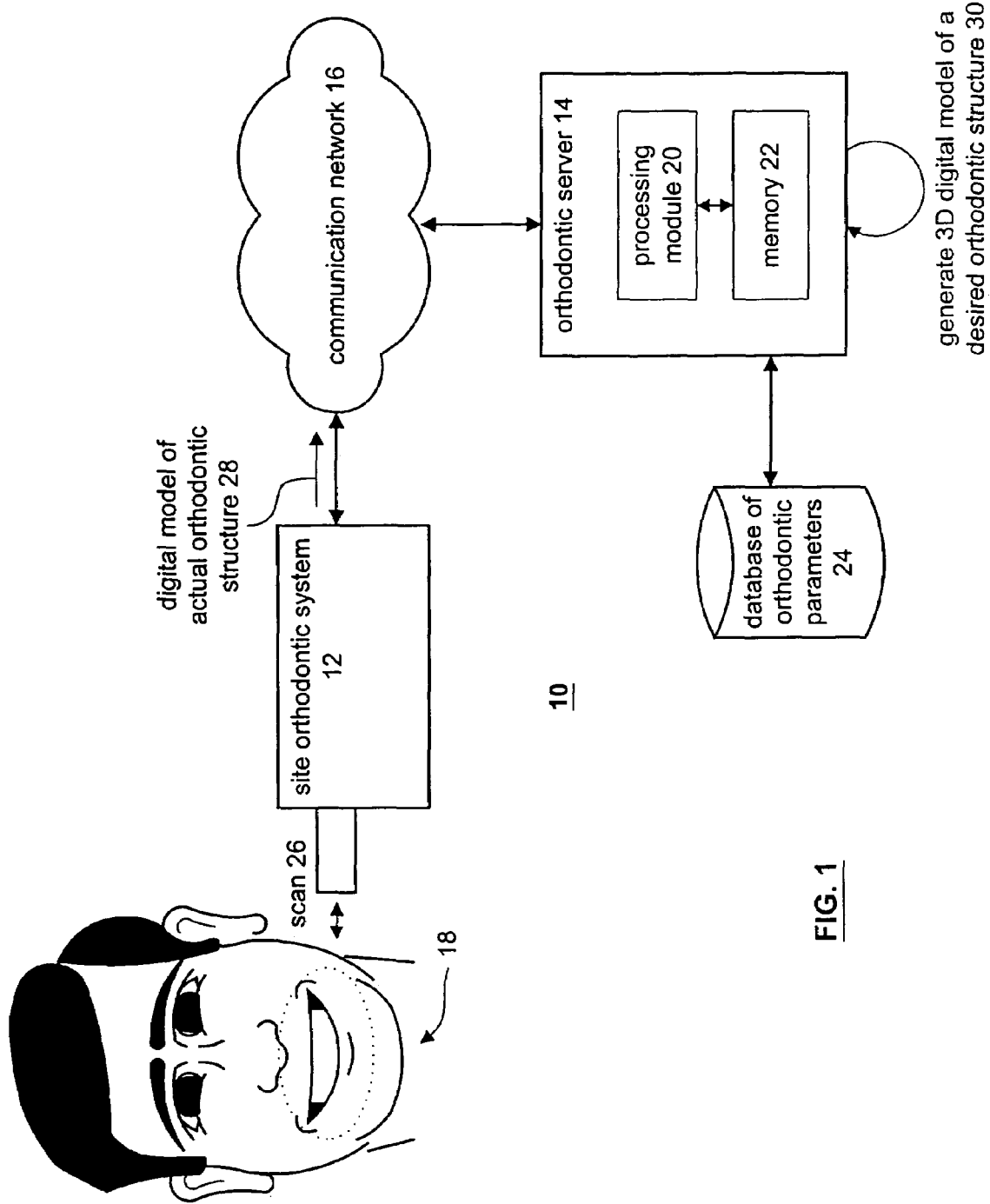
FIG. 1 illustrates a schematic block diagram of an orthodontic service system in accordance with the present invention.

The present invention can be more fully described with reference to FIGS. 1 through 7. FIG. 1 illustrates a schematic block diagram of an orthodontic servicing system 10 that includes a site orthodontic system 12, an orthodontic server 14, a communication network 16, and a database of orthodontic parameters 24. In operation, the site orthodontic system 12 scans 26 the patient's 18 orthodontic structure (i.e., teeth, gums, lips, upper and lower arches, and/or other facial features). The site orthodontic system 12 converts the scanned images of the orthodontic structure of the patient to use a digital model of the actual orthodontic structure 28. The orthodontic server 14 receives the digital model of the actual orthodontic structure 28 via the communication network 16. The communication network 16 may be a direct connect, the internet, local area network, wide area network, wide area network, and/or any device that enables the transference of digital information from one computing type system to another. Note that a specific embodiment of three-dimensional scanning is described in patent application Ser. No. 09/560,584 filed before the United States Patent Office on Apr. 28, 2000, and is hereby incorporated herein by reference.

The orthodontic server includes a processing module 20 and memory 22. The processing module 20 may be a single processing device or a plurality of processing devices. Such a processing device may be a microprocessor, microcomputer, microcontroller, digital signal processor, central processing unit, state machine, logic circuitry, and/or any device that manipulates signals (e.g., analog and/or digital) based on operational instructions. The memory 22 may be a single memory device or a plurality of memory devices. Such a memory device may be a read-only memory, random access memory, floppy disk memory, hard drive memory, system memory, flash memory, and/or any device that stores digital information. Note that when the processing model 20 implements one or more of its functions via a state machine or logic circuitry, the memory storing the corresponding operational instructions is embedded within the circuitry comprising the state machine and/or logic circuitry.

The orthodontic server 14 generates a three-dimensional digital model of the desired orthodontic structure 30 from the digital model of the actual orthodontic structure 28 and orthodontic parameters contained in the database of orthodontic parameters 24. To achieve this, the processing module 20 via operational instructions stored in memory 22, performs the processing steps which are discussed in greater detail in patent application, which is hereby incorporated by reference, entitled "Method and Apparatus for Generating a Desired Three-Dimensional Digital Model of an Orthodontic Structure" having a filing date of Nov. 30, 1999 and a Ser. No. 09/452,031, now U.S. Pat. No. 6,431,870. For a more detailed discussion of the site orthodontic system 12, the orthodontic server 14 and the database of orthodontic parameters refer to patent application, which is hereby incorporated by reference, entitled "Method and Apparatus for Determining and Monitoring Orthodontic Treatment" having a filing date of Nov. 30, 1999 and a Ser. No. 09/451,637, now U.S. Pat. No. 6,471,512, patent application, which is hereby incorporated by reference, entitled "Method and Apparatus for Treating an Orthodontic Patient filed on Nov. 30, 1999 having a Ser. No. 09/451,560, now U.S. Pat. No. 6,540,512, and patent application, which is hereby incorporated by reference, entitled "Method and Apparatus for Site Treatment of an Orthodontic Patient" having a filing date of Nov. 30, 1999 and a Ser. No. 09/452,038, now U.S. Pat. No. 6,315,553.

Figure 2:
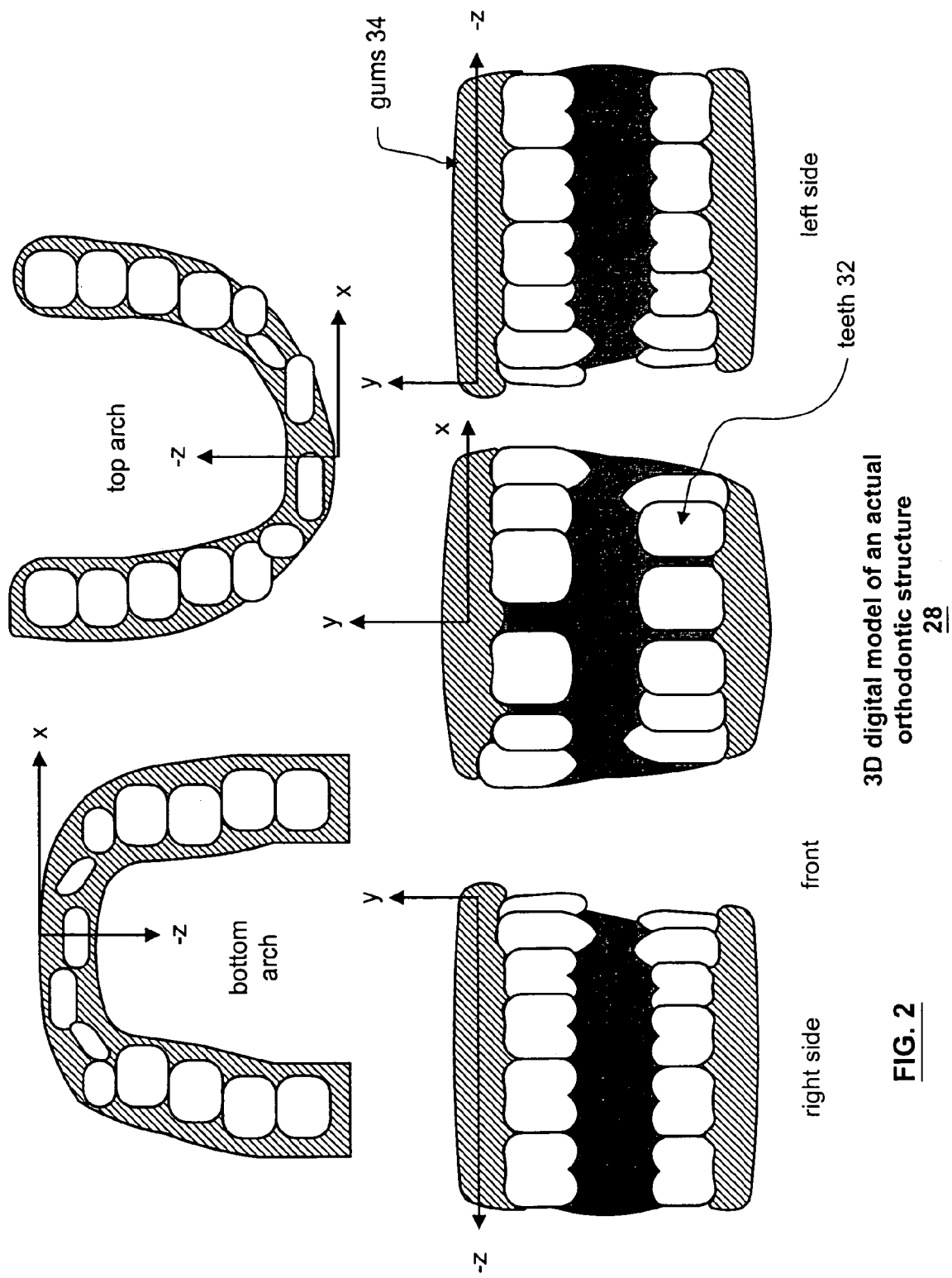
FIG. 2 illustrates a graphical representation of three-dimensional digital model of an actual orthodontic structure in accordance with the present invention.

FIG. 2 illustrates a graphical representation of the three-dimensional digital model of an actual orthodontic structure 28. As shown, the orthodontic structure is mapped to an X, Y, Z coordinate system. For a detailed discussion of the mapping of the digital model to an X, Y, Z coordinate system refer to patent application, which is hereby incorporated by reference, entitled "Method and Apparatus for Producing a Three-Dimensional Image of an Orthodontic Patient" filed on Nov. 30, 1999 and having a Ser. No. 09/452,034, abandoned. As shown, the three-dimensional model of the actual orthodontic structure 28 includes surface images of the teeth 32 and gums 34. The three-dimensional model may further include surface images of the bone structure, lips and other soft facial tissues. The generation of the three-dimensional digital model of the actual orthodontic structure is further described in the aforementioned patent application in this paragraph.

FIG. 3 illustrates a graphical representation of a virtual model of a patient's teeth having an orthodontic apparatus attached thereto with the orthodontic apparatus shown in dashed lines. The orthodontic apparatus includes a plurality of digitally placed brackets 40 and an ideal arch wire 38. Note that the term bracket, as used herein, includes a bracket, a band, head gear tube, or any device used to mount onto a patient's tooth for reception of a displacement apparatus such as an arch wire, rubber band, and/or head gear. As shown, the brackets 40 and arch wire 38 are positioned below, i.e., distally, of the gum and bone line 34. Each tooth, via the digitally placed brackets 40 and the ideal arch wire 38 will experience a force system causing the tooth to be repositioned in an optimal treatment manner. Optimal treatment includes factors such as shortest displacement distance, minimal number of wire changes, selection of brackets, cost, treatment time, patient discomfort tolerance, available appliances, etc. and can be digitally modeled to ensure that the force system is optimal from the outset of the treatment.

The force system that causes a tooth to move from its malocclusion position to its desired position has many contributing biological factors and mechanical factors. For example, the mechanical factors include peeling forces of the bonding agent, shear bond strength, ligation forces, wire characteristics, the type of adhesive used, anatomy of the tooth, bracket geometry, bracket slot geometry, bracket base configuration, arch wire shape, arch wire elasticity, arch wire diameter, and manufacturing tolerances. The biological factors include tooth interference, tooth anatomy, growth of the jaw, eruption of teeth, jaw function, root length, and periodontal characteristics. In accordance with the teachings of the present invention, each of these factors can be digitally simulated to determine a resulting force system. In addition, each contributing factor may be digitally altered to optimize the force system prior to any orthodontic appliances being installed on the patient's orthodontic structure. Note that each contributing factor to the force system may be stored in the database of orthodontic parameters 24 such that generic factors may be used for any given patient. Further note that the generic factors may be customized for each patient and/or custom factors may be newly created for each patient. As one of average skill in the art will appreciate, as long as a digital model of the patient's orthodontic structure is available, creation of digital models of the contributing factors of the force system may be readily obtained, derived, created, etc. As one of average skill in the art will further appreciate, the force system includes the effects of bonding pad thickness, bonding agent properties, the arch wire, ligation forces, and biological characteristics (e.g., growth, tooth interference, tooth anatomy). Each of these factors may be adjusted individually or in combination to optimize the force system.

A key factor in the force system is the bracket. FIGS. 4 and 5 illustrate various types of brackets. In particular, FIG. 4 illustrates a standard bracket or a generic prescription bracket 42 that includes a generic wire retention receptacle 46. For the standard bracket, the generic wire retention receptacle 46 is a simple groove (i.e., a slot) in the bracket 42 without complex angles or depths. For the generic prescription bracket 42, the generic wire retention receptacle 46 is a groove in the bracket 42 that includes a generic angularity of complex angles and grooves that have been normalized for semi-custom treatment. The arch wire 44 is inserted into the bracket as shown to provide the desired torque or force system on the corresponding tooth.

FIG. 5 illustrates a custom bracket 42 having a specific wire retention receptacle 48. In this embodiment, the bracket has a retention receptacle 48 designed to include complex angles of depth and groove that are determined for a particular patient. As such, the orthodontic apparatus applied to a patient's tooth may include brackets having generic arch wire retention receptacles 46 or brackets having specific wire retention receptacles 48.

FIG. 6 illustrates a graphical representation of a correction for an undercut condition. As is known, when the bracket 51 is placed on the tooth 55 such that a vertical line from the bracket intersects with the tooth 55, an undercut 57 condition exists. When an undercut 57 condition exists, it is difficult to install the bracket using a transfer tray, since, when the transfer tray is removed after the bracket as been bonded, it must be pulled off at an angle. By pulling the tray off at an angle, there is a risk of loosing, or pulling off, the bracket 51. To avoid the undercut 57 condition, the bonding agent thickness may be varied to provide the same force system as the bracket placement with the undercut 57. However, by modifying the position of the bracket, the undercut condition is avoided as are the associated difficulties.

Figure 7:
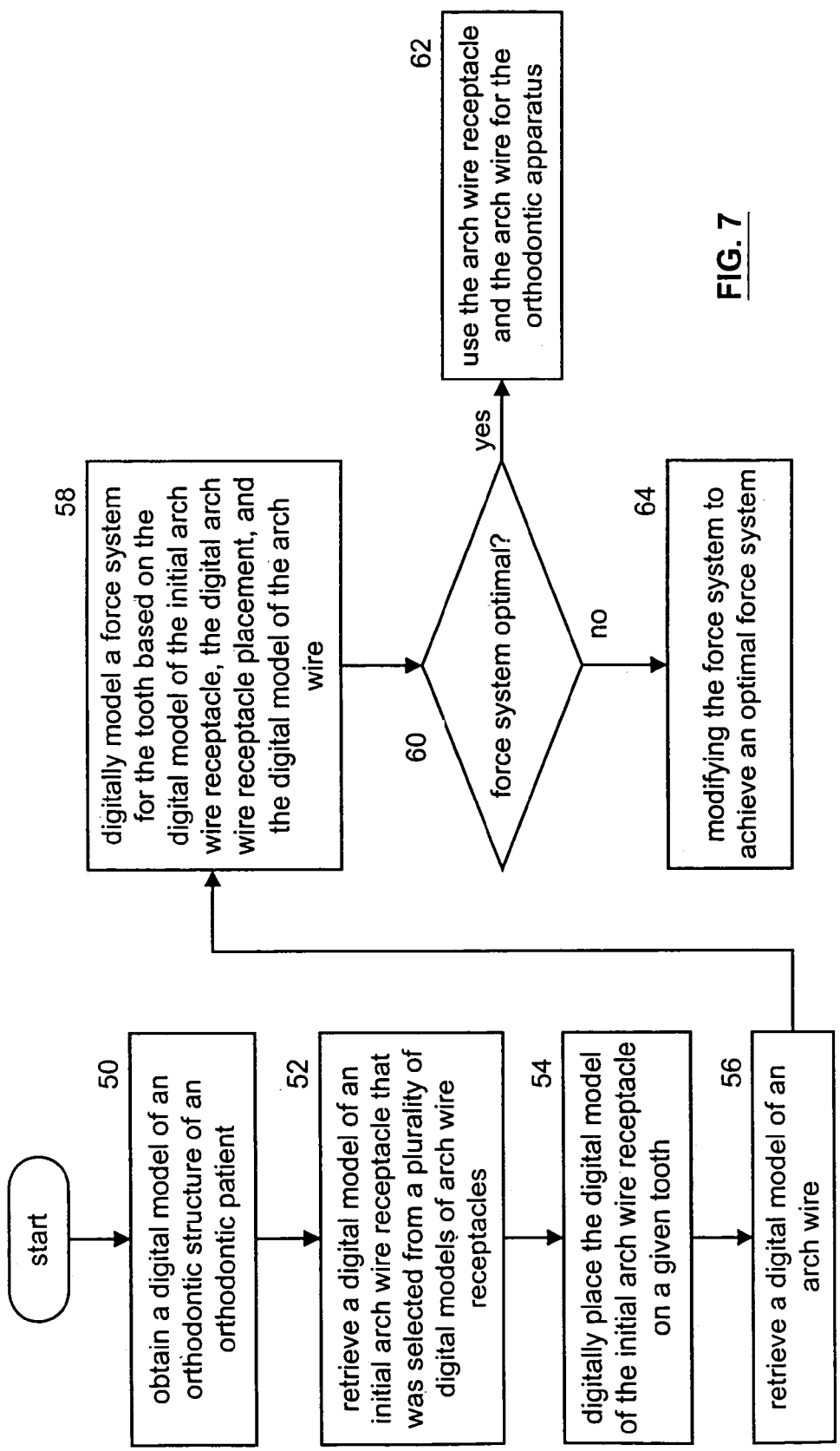
FIG. 7 illustrates a logic diagram of a method for arch wire receptacle optimization in accordance with the present invention.

FIG. 7 illustrates a logic diagram of a method for arch wire receptacle optimization. The process begins at step 50 where a digital model of an orthodontic structure of an orthodontic patient is obtained. The process then proceeds to step 52 where a digital model of an initial arch wire receptacle that was selected from a plurality of digital models of arch wire receptacles is retrieved. Note that the arch wire receptacle includes brackets, bands, and/or headgear tubes. The process then proceeds to step 54 where the digital model of the initial arch wire receptacle is digitally placed on a given tooth. The process then proceeds to step 56 where a digital model of an arch wire is retrieved. The process then proceeds to step 58 where a force system for the tooth is digitally modeled based on the digital model of the initial arch wire receptacle, the digital arch wire receptacle placement, and the digital model of the arch wire. Note that the determination of the force system may be based on a tooth to bonding agent force, a bonding agent to bracket force and a wire-to-bracket force. In essence, the force for each of these types of interactions is based on wire tensile strength, shape of the brackets, thickness of the bonding agent, and patient physical parameters and is readily determined using conventional mathematics, which can be digitally modeled as discussed.

The process proceeds to step 60 where a determination is made as to whether the force system is optimal. If so, the process proceeds to step 62 where the arch wire receptacle and the arch wire for the orthodontic apparatus are used. If the force system is not optimal, the process proceeds to step 64 where the force system is modified to obtain an optimal force system. Modifying the force system may include changing the bonding pad thickness, the bonding agent properties, the arch wire, ligation forces, and/or the brackets, selecting the characteristics of the arch wire, and/or reducing the force system requirements such that given orthodontic appliances may adhere to the desired force system. The modification of the force system may also be done by adjusting the functional loading on other teeth, adjusting the material of the initial arch wire receptacle and/or the arch wire. Alternatively, or in addition to, the force system may be modified by selecting different digital models of the arch wire receptacle and/or arch wire, adjusting the placement of the digital model of the initial arch wire receptacle, adjusting the bonding agent properties, thickness, type, etc. of the digital model of the initial arch wire receptacle, and/or by adjusting the bracket wire coupling of the digital model of the initial arch wire receptacle (e.g., change the slot on the bracket or placement of the bracket).

Figure 8:
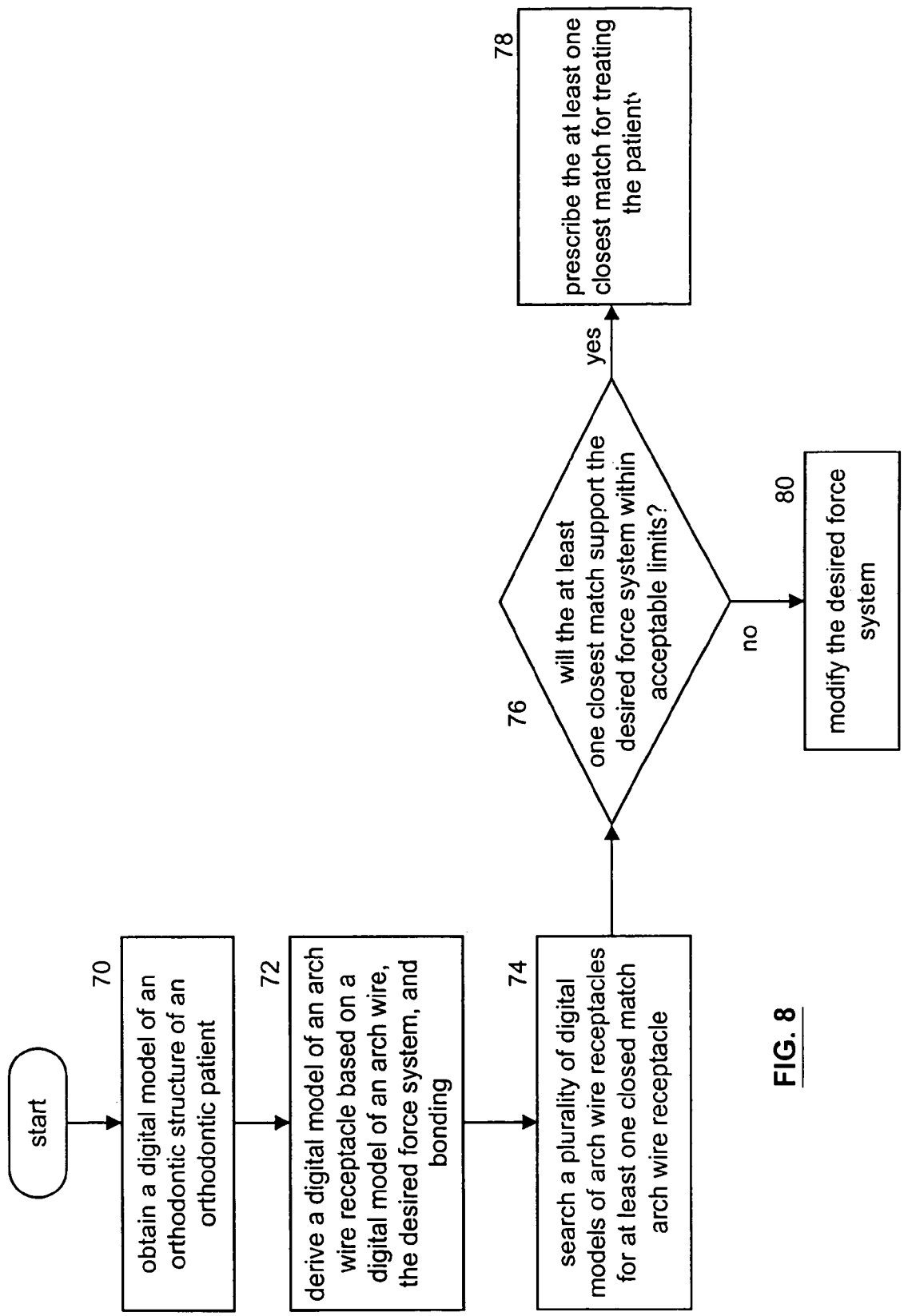
FIG. 8 illustrates a logic diagram of an alternate method for arch wire receptacle optimization in accordance with the present invention.

FIG. 8 illustrates a logic diagram of an alternate method for arch wire receptacle optimization. The process begins at step 70 where a digital model of an orthodontic structure of an orthodontic patient is obtained. The process then proceeds to step 72 where a digital model of an arch wire receptacle is derived based on digital model of an arch wire, the desired force system, and the bonding agent. The process then proceeds to step 74 where a plurality of digital models of arch wire receptacles is searched for a closest match arch wire receptacle. In other words, a search is performed to find an existing arch wire receptacle that achieves the desired force system. The process then proceeds to step 76 where a determination is made as to whether the closest match arch wire receptacle will support the desired force system within acceptable limits. The acceptable limits will be primarily left up to the orthodontist and such factors will be based on patient pain tolerance, treatment plan, length of treatment, costs, etc. If the closest match arch wire receptacle will support the desired force system, the process proceeds to step 78 where the closest match arch wire receptacle is prescribed for treating the patient.

If the closest match arch wire receptacle will not support the desired force system, the process proceeds to step 80. At step 80 the desired force system is modified. The desired force system may be modified by adjusting placement of the digital model of the arch wire receptacle, adjusting the bonding agent properties of the bonding of the bracket to the teeth, adjusting the bracket wire coupling (i.e., the slot of the digital model of the arch wire receptacle, bracket placement, and/or adjusting the material of the arch wire receptacle and/or of the arch wire).

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes) can be simulated to determine appropriate treatment changes. Such compensation in treatment is not possible using prior methods which were based upon assumptions from a single model that the tooth movement would progress in a known manner. Therefore, the prior art methods would specify a single static treatment based upon this assumption. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, the treatment can be monitored and adjusted as needed by the system in an efficient manner. As such, unexpected tooth movement, such as occurs when a patient does not cooperate, or through biological changes, can be readily controlled.

The preceding discussion has presented a method and apparatus for optimizing arch wire receptacles. With such a method and apparatus, the focal point of orthodontic treatment is not hinged on the particular brackets used. As such, given the desired treatment plan, an appropriate bracket may be selected utilizing the teachings of the present invention. As one of average skill in the art would readily appreciate, other embodiments may be derived from the teaching of the present invention without deviating from the scope of the claims.

What is claimed is:

1. An orthodontic servicing system for selecting suitable generic archwire receptacle and bonding agent for treating an orthodontic patient, comprising:

a site orthodontic system; wherein said site orthodontic system scans the patient's orthodontic structure and converts the scanned images of the orthodontic structure to a digital model of the orthodontic structure; wherein said digital model of the orthodontic structure comprises teeth, gums, lips, upper and lower arches, and/or other facial features;

a communication network; and an orthodontic server; wherein said orthodontic server comprises a processing module; and memory operably coupled to the processing module; wherein the memory stores operational instructions that causes, or with the assistance of a user of said processing module enables, the processing module to (a) receive said digital model of the orthodontic structure from said site orthodontic system via said communication network; wherein said site orthodontic system and said orthodontic server are operably connected with each other over said communication network; (b) select, through digital simulation, a desired combination of a digital model of an arch wire receptacle, from a plurality of generic digital models of archwire receptacles, digital placement of said digital model of an arch wire receptacle on one or more of said teeth; wherein one archwire receptacle is placed on one tooth, and the bonding agent thickness based on said digital model of the orthodontic structure, a digital model of an arch wire, a desired force system, and the bonding agent properties; wherein said bonding agent is used to secure an archwire receptacle to a given tooth of the orthodontic structure; and (c) (i) increase said bonding agent thickness such that a digitally drawn vertical line from said model of an arch wire receptacle does not intersect the tooth to which said model of an arch wire receptacle is attached; and (ii) adjust the placement of said digital model of an arch wire receptacle on said tooth to which said model of an arch wire receptacle is attached in order to realize said desired force system.

2. The orthodontic servicing system of claim 1, wherein said processing module comprises a single processing device or a plurality of processing devices, wherein said processing device comprises a microprocessor, microcomputer, microcontroller, digital signal processor, central processing unit, state machine, logic circuitry, and/or any device that manipulates signals (e.g., analog and/or digital) based on operational instructions, and wherein said memory comprises a single memory device or a plurality of memory devices, wherein said memory device comprises a read-only memory, random access memory, floppy disk memory, hard drive memory, system memory, flash memory, and/or any device that stores digital information.

3. The orthodontic servicing system of claim 1, wherein said communication network comprises a direct connect, the internet, local area network, wide area network, and/or any device that enables the transference of digital information from one computing type system to another.

4. The orthodontic servicing system of claim 1, wherein said digital simulation comprises treatment planning and includes consideration of factors such as shortest displacement distance, minimal number of wire changes, selection of archwire receptacles, cost, treatment time, patient discomfort tolerance, and available appliances.

5. The orthodontic servicing system of claim 1, wherein said force system causes a tooth to move from its malocclusion position to its desired position, and wherein said force system has many contributing mechanical factors and biological factors.

6. The orthodontic servicing system of claim 5, wherein said mechanical factors include peeling forces of the bonding agent, shear bond strength, ligation forces, wire characteristics, the type of adhesive used, anatomy of the tooth, bracket geometry, bracket slot geometry, bracket base configuration, arch wire shape, arch wire elasticity, arch wire diameter, and manufacturing tolerances.

7. The orthodontic servicing system of claim 5, wherein said biological factors include tooth interference, tooth anatomy, growth of the jaw, eruption of teeth, jaw function, root length, and periodontal characteristics.

8. The orthodontic servicing system of claim 5, wherein said each contributing factor to said force system is stored in a database of orthodontic parameters such that generic factors are used for any given patient; wherein said orthodontic server is operably connected with said database of orthodontic parameters.

9. The orthodontic servicing system of claim 8, wherein said generic factors are customized for each patient and/or custom factors are newly created for each patient.

10. The orthodontic servicing system of claim 1, wherein said force system includes the effects of bonding agent, arch wire, ligation forces, and biological characteristics; wherein said biological characteristics include growth, tooth interference and tooth anatomy.

* * * * *